US006214101B1

(12) United States Patent
Nakaseko

(10) Patent No.: US 6,214,101 B1
(45) Date of Patent: Apr. 10, 2001

(54) PASTE-TYPE DENTAL GLASS IONOMER CEMENT COMPOSITION

(75) Inventor: Hisashi Nakaseko, Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 09/244,638

(22) Filed: Feb. 4, 1999

(30) Foreign Application Priority Data

Feb. 18, 1998 (JP) ................................... 10-051264

(51) Int. Cl.[7] ................................ A61K 6/08; C08R 2/48
(52) U.S. Cl. ......................... 106/35; 523/116; 433/228.1
(58) Field of Search .............................. 106/35; 523/116; 433/228.1

(56) References Cited

U.S. PATENT DOCUMENTS 5,063,257 * 11/1991 Akahane et al. .................... 523/116
5,520,725 * 5/1996 Kato et al. ............................ 106/35

* cited by examiner

Primary Examiner—C. Melissa Koslow
(74) Attorney, Agent, or Firm—Oblon, Spivak, McClelland, Maier & Neustadt, P.C.

(57) ABSTRACT

A paste-type dental glass ionomer cement composition is disclosed as comprising a first paste comprising an α-β unsaturated carboxylic acid polymer, water, and a filler not reactive with the α-β unsaturated carboxylic acid polymer; and a second paste comprising a fluoroaluminosilicate glass powder and a polymerizable monomer free of an acid group, wherein at least one of the first paste and the second paste contains a polymerization catalyst. By employing a construction such that a dental glass ionomer cement composition comprising a powder component and a liquid component is made pasty, the invention makes it possible to achieve the mixing by a easy operation, whereby both of the first paste and the second paste are mixed with each other to achieve curing of the composition.

11 Claims, No Drawings

PASTE-TYPE DENTAL GLASS IONOMER CEMENT COMPOSITION

FILED OF THE INVENTION

The present invention relates to a dental glass ionomer cement. More particularly, it relates to a paste-type dental glass ionomer cement composition comprising a first paste and a second paste, the both being cured upon mixing with each other.

BACKGROUND OF THE INVENTION

Many types of dental cements have become available and used in a wide range of applications. Representative examples of dental cements which are mainly used at present include zinc phosphate cements which utilize a reaction between zinc oxide and phosphoric acid; polycarboxylate cements which utilize a reaction between zinc oxide and a polycarboxylic acid; zinc oxide-eugenol cements which utilize a reaction between zinc oxide and eugenol; glass ionomer cements which utilize a reaction between a fluoroaluminosilicate glass powder and a polycarboxylic acid; and resin cements which utilize a polymerization of an acrylic monomer.

Each of these dental cements has merits and demerits. For instance, the zinc phosphate cements have no adhesive properties to a tooth structure and possess irritation of phosphoric acid at the initial stage of the curing; the polycarboxylate cements are low in the final strength of a cured product; and since the zinc oxide-eugenol cements are low in the strength and inferior in the intraoral durability, their use is limited to the temporary sealing, and the eugenol per se possess irritation. Also, though the resin cements have merits such as superior adhesive properties and high mechanical strength unlike other dental cements, they involve such defects that their operation is complicated and that their bioaffinity is questionable.

On the other hand, the glass ionomer cements are quite good in the affinity to living bodies and have good dentinal adhesive properties. Moreover, they are expected to have a caries preventing effect by the fluorine contained in the glass. While utilizing these many characteristic features, the glass ionomer cements are used in a wide range of applications such as filling and restoration of caries cavity; cementing of, for example, a crown, an inlay, a bridge, or an orthodontic band; lining of cavity; core construction; and pit and fissure sealing.

In addition, there are presently developed resin-reinforced glass ionomer cements in which the brittleness of a matrix by water at the time of the initial curing, which has hitherto been considered to be a disadvantage, is prevented, and the physical properties such as mechanical strengths, e.g., bending strength, and adhesive strength to a tooth structure are improved, and which have superior adhesive properties to dental metals, resins, porcelains, etc., upon addition of a polymerizable resin component to the liquid component of the glass ionomer cement.

As described above, the glass ionomer cements have various characteristic features. However, the conventional dental glass ionomer cements are constructed from a powder component and a liquid component and involve a drawback such that the operations such as weigh and mixing are complicated. The operation of mixing of a powder component with a liquid component is usually carried out on an exclusive mixing paper by using a spatula. However, at this time, since the powder component and the liquid component are not compatible with each other, the collected powder component is divided into two parts or four parts, which are then successively mixing with the liquid component. That is, the mixing operation is required such that the powder component and the liquid component are mixed with each other uniformly as far as possible. In addition, the mixing operation must be carried out within a short period of time, and in order to fully exhibit the characteristics of the materials to be used, a remarkably skilled technique is needed.

SUMMARY OF THE INVENTION

An object of the present invention is to overcome the defects of the conventional glass ionomer cements as described above and to provide a paste-type dental glass ionomer cement composition in which mixing is possible by a easy operation, through a construction such that a dental glass ionomer cement composition comprising a powder component and a liquid component is made pasty, whereby both of a first paste and a second paste are mixed with each other to achieve curing of the composition.

In order to achieve the above-described object, I, the present inventor, made extensive and intensive investigations. As a result, I have completed a paste-type dental glass ionomer cement composition which does not require a technical skill for mixing operation, through a paste-type dental glass ionomer cement composition having a construction comprising a first paste prepared by combining an $\alpha$-$\beta$ unsaturated carboxylic acid polymer, water and a filler not reactive with the $\alpha$-$\beta$ unsaturated carboxylic acid polymer; and a second paste prepared by combining a fluoroaluminosilicate glass powder and a polymerizable monomer free of an acid group, wherein at least one of the first paste and the second paste contains a polymerization catalyst.

DETAILED DESCRIPTION OF THE INVENTION

That is, the paste-type dental glass ionomer cement composition according to the present invention is characterized in that:

the first paste comprises (a) an $\alpha$-$\beta$ unsaturated carboxylic acid polymer, (b) water, and (c) a filler not reactive with the above-described $\alpha$-$\beta$ unsaturated carboxylic acid polymer; and the second paste comprises (d) a fluoroaluminosilicate glass powder and (e) a polymerizable monomer free of an acid group; and at least one said first paste and said second paste contains (f) a polymerization catalyst.

In this case, from the point of view of the mixing operation of the paste-type dental glass ionomer cement composition, it is preferred that the first paste comprises from 20 to 60% by weight of an $\alpha$-$\beta$ unsaturated carboxylic acid polymer, from 20 to 60% by weight of water, and from 10 to 60% by weight of a filler not reactive with the above-described $\alpha$-$\beta$ unsaturated carboxylic acid polymer; and the second paste comprises from 50 to 85% by weight of a fluoroaluminosilicate glass powder and from 15 to 50% by weight of a polymerizable monomer free of an acid group and that at least one of the first paste and the second paste contains a polymerization catalyst in an amount in total of from 0.05 to 10% by weight based on a total amount of the paste-type dental glass ionomer cement composition in mixing for using the first paste and the second paste.

The $\alpha$-$\beta$ unsaturated carboxylic acid polymer as the component (a) to constitute the first paste is a homopolymer or copolymer of at least one member selected from acrylic acid, methacrylic acid, 2-chloroacrylic acid, 3-chloroacrylic acid, aconitic acid, mesaconic acid, maleic acid, itaconic acid, fumaric acid, glutaconic acid, and citraconic acid and is preferably a polymer not containing a polymerizable ethylenically unsaturated double bond and having a weight average molecular weight of from 5,000 to 40,000. In these α-β unsaturated carboxylic acid polymers, in case that a polymer having a weight average molecular weight of less than 5,000, not only the strength of a cured product tends to become low, but also the adhesive strength to a tooth structure is liable to be lowered. In case that a polymer having a weight average molecular weight exceeding 40,000 is used, the consistency at the time of mixing is too high, whereby the mixing tends to become difficult. A proportion of the α-β unsaturated carboxylic acid polymer in the first paste is preferably from 20 to 60% by weight. If the proportion is less than 20% by weight, the adhesive strength to a tooth structure which are a characteristic as the dental glass ionomer cement are liable to be lowered, whereas if it exceeds 60% by weight, the solubility of a cured product tends to increases so that the durability is liable to be inferior.

The water as the component (b) to constitute the first paste is an indispensable component in the present invention. This is because the acid-base reaction between the fluoroaluminosilicate glass and the α-β unsaturated carboxylic acid polymer proceeds in the presence of water. Further, the paste-type dental glass ionomer cement composition according to the present invention adheres to a surface of a teeth in the presence of water. Thus, the water is always present in the composition according to the present invention and is preferably used in a range of 20~60% by weight. If the proportion of the water is less than 20% by weight, the adhesive strength to the tooth structure which are a characteristic of the dental glass ionomer cement are liable to be lowered, whereas if it exceeds 60% by weight, the physical properties of a cured product tend to be lowered.

Specific examples of the filler not reactive with the α-β unsaturated carboxylic acid polymer as the component (c) to constitute the first paste is selected from silica sand, quartz, colloidal silica, feldspar, alumina, strontium glass, barium glass, borosilicate glass, kaolin, talc, calcium carbonate, calcium phosphate, titania, and barium sulfate. Besides, composite fillers prepared by pulverizing a polymer containing such inorganic fillers can also be used. As a matter of course, mixtures of two or more of these inorganic fillers may be used. In the composition according to the present invention, the filler not reactive with the α-β unsaturated carboxylic acid polymer preferably has a mean particle size of 0.02~10 μm and is used in a proportion of 10~60% by weight in the first paste. In case that the mean particle size of the filler exceeds 10 μm, the surface smoothness of the cured product is not good on the one hand. On the other hand, in case that a fine powder having a mean particle size of smaller than 0.02 μm is used, a requisite amount of the powder is hardly incorporated into the composition, whereby the physical properties are liable to be lowered. Further, if the proportion of the filler is less than 10% by weight, effects such as an increase in physical properties are difficult to be obtained generally, whereas if it exceeds 60% by weight, the first paste becomes so stiff that the mixing with the second paste is difficult, and the physical properties are also liable to be lowered. In this case, the use of organic fillers such as polymethyl acrylate, polymethyl methacrylate, polyethyl acrylate, polyethyl methacrylate, ethylene-vinyl acetate copolymer is not restricted but may be properly mixed and used.

The fluoroaluminosilicate glass powder as the component (d) to constitute the second paste is preferably a fluoroaluminosilicate glass powder having a mean particle size of 0.02~10 μm and a specific gravity of 2.4~4.0 and containing $Al^{3+}$, $Si^{4+}$, $F^-$, and $O^{2-}$ as the major components and further containing $Sr^{2+}$ and/or $Ca^{2+}$. In case that the mean particle size exceeds 10 μm on the one hand, since no surface smoothness of the cured product is obtained. On the other hand, in case that the mean particle size is smaller than 0.02 μm, a requisite amount of the powder is difficult to be incorporated into the composition, whereby the physical properties are liable to be lowered. The particle size can be measured by usual means and is expressed in terms of a mean value of the major axis and the minor axis. In the fluoroaluminosilicate glass powder, it is preferred that the proportions of $Al^{3+}$, $Si^{4+}$, $F^-$ and a sum of $Sr^{2+}$ and $Ca^{2+}$ are from 10 to 21% by weight, from 9 to 24% by weight, from 1 to 20% by weight, and from 10 to 34% by weight, respectively based on the total weight of the glass. These proportions of the major components greatly influence the operability and physical properties such as curing rate, final strength, and solubility. If the proportion of $Al^{3+}$ is less than 10% by weight, the curing rate is slow, and the strength is liable to be low, whereas if it exceeds 21% by weight, the preparation of a glass is difficult, and the transparency becomes lowered, whereby the esthetics tend to be inferior. In case that the proportion of $Si^{4+}$ is less than 9% by weight, the preparation of a glass is liable to be difficult, whereas in case that it exceeds 24% by weight, the curing rate tends to be slow, and the strength is lowered, whereby the durability is liable to be of problem. If the proportion of $F^-$ is less than 1% by weight, a working time of the cement composition is short, whereby the operation for use tends to be difficult, whereas if exceeds 20% by weight, not only the setting time is long, but also the solubility in water is so high that the durability tends to be inferior. If the sum of $Sr^{2+}$ and $Ca^{2+}$ is less than 10% by weight, the sharpness of curing is not exhibited, whereby the curing rate tends to be slow. Also, in this case, the preparation of a glass is liable to be difficult. If the sum of $Sr^{2+}$ and $Ca^{2+}$ exceeds 34% by weight, the working time is so short that the curing rate is too fast, whereby the actual use is liable to be difficult. In this case, the solubility in water is so high that the durability is likely lowered.

The fluoroaluminosilicate glass which is used in the present invention can be prepared by known preparation processes of a glass. Also, it is preferred that the fluoroaluminosilicate glass powder is present in the second paste in a proportion from 50 to 85% by weight. If the proportion of the fluoroaluminosilicate glass powder is less than 50% by weight, the physical properties of a cured product may be inferior, whereas if it exceeds 85% by weight, the second paste is so stiff that the operability at the time of mixing tends to become poor.

The polymerizable monomer free of an acid group as the component (e) to constitute the second paste is compounded to prevent the brittleness of a matrix by water at the time of the initial curing, which has hitherto been considered to be a disadvantage for the conventional glass ionomers, and to improve the physical properties such as mechanical strength, e.g., bending strength, and adhesive strength to a tooth structure. The polymerizable monomer free of an acid group is a polymerizable unsaturated compound containing at least one $CH_2=CR-COO-$ group, wherein R is H or $CH_3$ and refers to a polymerizable unsaturated compound containing an acryloid group or a methacryloid group, such as esters of acrylic acid or methacrylic acid, and is required not to be reactive with the fluoroaluminosilicate glass. That is, this polymerizable monomer does not contain an acid group reactive with the fluoroaluminosilicate glass powder, such as an acid group containing a carboxylic acid, phosphoric acid, sulfuric, or boric acid. Also, the polymerizable monomer free of an acid group is not limited thereto but preferably contains no acid group to undergo an acid-base reaction with the glass powder.

The proportion of the polymerizable monomer free of an acid group is preferably in a range of 15~50% by weight in the second paste. If the proportion of the polymerizable monomer free of an acid group is less than 15% by weight, the initial curing properties and physical characteristics are likely inferior, whereas if it exceeds 50% by weight, the adhesive strength to a tooth structure as a characteristic of the glass ionomer cement are liable to be inferior.

Further, the present invention includes an embodiment in which a surface of the fluoroaluminosilicate glass powder as the component (d) of the second paste or of the filler not reactive with the α-β unsaturated carboxylic acid polymer as the component (c) of the first paste is modified with a polymerizable ethylenically unsaturated double bond-containing organic compound. This modifying enables to improve the final strength of a cured product and is useful for the stability of a dental cement in an oral cavity. It is preferred that a powder component such as the fluoroaluminosilicate glass powder or the filler not reactive with the α-β unsaturated carboxylic acid polymer is covered by the polymerizable ethylenically unsaturated double bond-containing organic compound in an amount of 0.01 to 20 parts by weight based on 100 parts by weight of the powder component. Examples of the polymerizable ethylenically unsaturated double bond-containing organic compound which can be used for this surface modifying include vinyl-based silane coupling agents such as vinyl trimethoxysilane, vinyl triethoxysilane, γ-methacryloxypropyl trimethoxysilane, γ-methacryloxypropylmethyl dimethoxysilane, and vinyl trichlorosilane and vinyl tris(2-methoxyethoxy)silane; and unsaturated carboxylic acids such as methacrylic acid, acrylic acid, and maleic acid.

In the dental paste-type dental ionomer cement composition according to the present invention, chemical polymerization catalysts or photopolymerization catalysts are used as the polymerization catalyst as the component (f) for polymerizing the polymerizable monomer free of an acid group. These catalysts are contained in at least one of the first and second pastes and used singly or in admixture depending upon the application of the paste-type dental glass ionomer cement. Also, from the point of view of the curing mechanism of the paste-type dental glass ionomer cement composition, a mixing ratio of the first paste to the second paste to be mixed for the paste-type dental glass ionomer cement composition is preferably from 5:1 to 1:10, and particularly from 4:1~1:5 by weight.

In case that the paste-type dental glass ionomer cement composition according to the present invention is used for applications in which the paste-type dental glass ionomer cement composition is difficult to be subjected to enough irradiation with a light, as in, for example, cementing of an inlay or a crown, chemical polymerization catalysts such as organic aromatic compounds containing at least one —$SO_2$— group, e.g., aromatic sulfinic acids or alkaline salts thereof, or aromatic sulfonyl compounds, can be used. Specific examples thereof include sodium p-toluenesulfinate, lithium p-toluenesulfinate, benzenesulfinic acid, sodium benzenesulfinate, p-toluenesulfonyl chloride, p-toluenesulfonyl fluoride, o-toluenesulfonyl isocyanate, and sodium p-acetamidobenzenesufinate, with sodium p-toluenesulfinate and sodium benzenesulfinate being preferred. These organic aromatic compounds containing at least one —$SO_2$— group may be used in the form of a salt hydrate. However, since when these chemical polymerization catalysts are compounded together with the polymerizable monomer free of an acid group, they have an action to cure the polymerizable monomer free of an acid group, they must be compounded in the first paste. In addition, since when these polymerization catalysts are stored under high-humidity conditions for a long period of time, they may likely cause decomposition or oxidation, the polymerization catalysts are encapsulated by polymeric compounds such as cellulose, whereby the stable shelf stability can be kept over a long period of time. The encapsulation of the chemical polymerization catalyst makes it possible to compound the chemical polymerization catalyst in not only the first paste but also the second paste through a proper selection of the polymeric compound. However, in the encapsulation of the chemical polymerization catalyst in the present invention, it is preferred to use a water-insoluble polymeric compound and compound it in the first paste. This is because in general, water-insoluble polymeric compounds exhibit stable shelf stability under high-humidity conditions as compared with water-soluble polymeric compounds.

Examples of the water-insoluble polymeric compound which can be used for encapsulation of the polymerization catalyst include ethyl cellulose, cellulose acetate, polyvinyl formal, cellulose acetate phthalate, cellulose acetate butyrate, hydroxypropylmethyl cellulose phthalate, and Eudragit. Examples of the water-soluble polymeric compound include polyvinyl alcohol, carboxymethyl cellulose, methyl cellulose, and hydroxyethyl cellulose. In order that the encapsulated catalyst is dispersed in the paste and has a disintegration property as much as possible, the encapsulated catalyst preferably has a mean particle size ranging from 0.1 to 30 μm. If the mean particle size is smaller than 0.1 μm, the encapsulation is hardly achieved, whereas if it exceeds 30 μm, the dispersibility in the paste tends to be poor.

In the paste-type dental glass ionomer cement composition according to the present invention, for applications of sufficient irradiation with a light to the paste-type dental glass ionomer cement composition, such as when it is used for filling a caries cavity, a photopolymerization catalyst is used instead of the chemical polymerization catalyst, and the polymerizable monomer free of an acid group is polymerized by a visible light. Thus, it becomes possible to initiate to cure the paste-type dental glass ionomer cement composition at any timing when an operator desires until the acid-base reaction between the fluoroaluminosilicate glass powder and the α-β unsaturated carboxylic acid polymer has completed. In this case, as the photopolymerization catalyst, a combination of a sensitizing agent with a reducing agent is generally used. As the sensitizing agent, those which can polymerize the polymerizable monomer by the action of a visible light having a wavelength of from 390 nm to 830 nm are used. Examples thereof include camphorquinone, benzil, diacetyl, benzyl dimethyl ketal, benzyl diethyl ketal, benzyl di(2-methoxyethyl) ketal, 4,4,'-dimethylbenzyl dimethyl ketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropyl thioxanthone, 2-nitrothioxanthone, 2-methyl thioxanthone, 2,4-dimethyl thioxanthone, 2,4-diethyl thioxanthone, 2,4-diisopropyl thioxanthone, 2-chloro-7-trifluoromethyl thioxanthone, thioxanthone-10,10-dioxide, thioxanthone-10-oxide, benzoin methyl ether, benzoin ethyl ether, isopropyl ether, benzoin isobutyl ether, benzophenone, bis(4-dimethylaminophenyl)ketone, 4,4,'-bisdiethylaminobenzophenone, acyl phosphine oxides such as (2,4,6-trimethylbenzoyl)diphenylphosphine oxide, and azide-containing compounds. These compounds may be used singly or in admixture.

As the reducing agent, tertiary amines and the like are generally used. Suitable examples of the tertiary amines include N,N-dimethyl-p-toluidine, N,N-dimethylaminoethyl methacrylate, triethanolamine, methyl 4-dimethylaminobenzoate, ethyl 4-dimethylaminobenzoate, and isoamyl 4-dimethylaminobenzoate. As other reducing agents, sodium sulfinate derivatives and orgnometallic compounds can also be used. These compounds may be used singly or in admixture.

Since these sensitizing agent and the reducing agent do not generally have an action to cure the polymerizable monomer free of an acid group prior to the irradiation with a light, and the sensitizing agents or the reducing agents do not react with each other, they can be compounded in any of the first and second pastes. Also, the sensitizing agent and the reducing agent can be compounded either individually or simultaneously. Incidentally, like the above-described chemical polymerization catalyst, of the photopolymerization catalysts, ones having a direct action to polymerize the polymerizable monomer free of an acid group are compounded in the first paste and upon encapsulation through selection of a proper polymeric compound, can be compounded in not only the first paste but also the second paste. However, even in this case, when a water-insoluble polymeric compound is used and compounded in the first paste, a stable shelf stability can be given over a longer period of time.

In the paste-type dental glass ionomer cement composition according to the present invention, the chemical polymerization catalyst and the photopolymerization catalyst can be used in combination. By the use of the chemical polymerization catalyst and the photopolymerization catalyst in combination, a glass ionomer cement composition having a so-called triple-curing reaction system is obtained by an photopolymerization reaction by the irradiation with a visible light, in addition to the rapid polymerization reaction of the polymerizable monomer by the chemical polymerization and the acid-base reaction between the fluoroaluminosilicate glass powder and the $\alpha$-$\beta$ unsaturated carboxylic acid polymer. In this case, if desired, a method in which the photopolymerization and the chemical polymerization are used properly, for example, a method in which the chemical polymerization and photopolymerization are applied for filling a caries cavity, whereas the chemical polymerization is applied for cementing an inlay or a crown, can be employed so that a further enlargement of the application can be expected. In case where the chemical polymerization catalyst and the photopolymerization catalyst are used in combination, the restrictions in compounding of each of the catalysts follow the above description. Also, in the paste-type dental glass ionomer cement composition according to the present invention, a polymerization inhibitor, a ultraviolet absorber, and the like which are usually employed can be properly compounded, if desired.

In case where the photopolymerization catalyst is used, the polymerization reaction of the polymerizable monomer free of an acid group is achieved by irradiation with actinic radiations such as an ultraviolet light or a visible light. Examples of light sources which can be used include various mercury vapor-pressure lamps including ultrahigh-, high-, medium- and low-pressure ones, a chemical lamp, a carbon arc lamp, a metal halide lamp, a fluorescent lamp, a tungsten lamp, a xenon lamp, and an argon ion laser.

In case where the polymerization catalyst is compounded in at least one of the pastes, the total amount of the catalysts is preferably in a range of 0.05~10% by weight based on the total amount of the paste-type dental glass ionomer cement composition when the first paste and the second paste are mixed for using. If the total amount of the catalysts is less than 0.05% by weight, sufficient curing characteristics are liable to be not obtained, whereas even if it exceeds 10% by weight, the curing characteristics are not particularly improved.

The present invention is described in detail with reference to the following Examples. It is not to be construed that the present invention is limited to these Examples.

EXAMPLE 1

The following components were mixed to prepare a first paste.

| Component (a): | Acrylic acid-maleic acid copolymer having a weight average molecular weight of 18,000 | 42% by weight |
|---|---|---|
| Component (b): | Distilled water | 42% by weight |
| Component (c): | Silane-modified silica sand powder [prepared by adding 20 g of a 10% vinyl ethoxysilane-ethyl alcohol solution to 100 g of fine powdered silica sand having a mean particle size of 4 $\mu$m, stirring the mixture in a mortar, and then drying it a 100° C. for 2 hours by a vapor dryer] | 11% by weight |
| Component (f): | Sodium benzenesulfinate | 5% by weight |

The following components were mixed to prepare a second paste.

| Component (d): | Silane-modified fluoro-aluminosilicate glass powder [prepared by mixing 22 g of aluminum oxide, 43 g of silicic anhydride, 12 g of calcium fluoride, 15 g of calcium phosphate, and 8 g of strontium carbonate; keeping the mixture in a high-temperature electric furnace at 1,200° C. for 5 hours to melt a glass; after cooling, pulverizing the product in a ball mill for 10 hours; passing the pulverized product through a 200-mesh (ASTM) sieve to form a glass powder; mixing 100 g of the glass powder with 20 g of a 10% $\gamma$-methacryloyloxypropyl trimethoxysilane-ethyl alcohol | 73% by weight |

| | -continued | |
|---|---|---|
| | solution in a mortar; and then drying it at 110° C. for 2 hours by a vapor dryer] | |
| Component (e): | Hydroxyethyl methacrylate | 15% by weight |
| | 2-hydroxy-1-acryloxy-3-methacryloxypropane | 4% by weight |
| | Di-2-methacryloxyethyl-2,2,4-triethylhexamethylene dicarbamate | 4% by weight |
| | Glycidyl methacrylate | 4% by weight |

0.8 g of the first paste and 2.3 g of the second paste were weighed and mixed for 10 seconds by using a mixed paper and a spatula. As a result, a working time at room temperature of 23° C. was 2 minutes and 25 seconds. The same mixing operation was carried out, and the following tests were carried out. The results obtained are shown in Table 1. The numerical values given are a mean value and a standard deviation with respect to ten samples.

(Working Time)

The working time was evaluated by touching a cement mixture by a tip of a spatula, and measuring a time until the fluidity of the cement mixture had been lost.

(Bending Strength Test)

A sample after mixing was filled in an acrylic resin-made tube having an inner diameter of 3 mm and a length of 25 mm and press contacted by using a glass sheet via cellophane, to obtain ten cylindrical cured materials. The obtained test pieces were immersed in distilled water at 37° C. for 24 hours and then subjected to a bending strength test by three-point bending by means of an autograph (made by Shimadzu Corporation) at a span of 20 mm and at a crosshead speed of 1 mm/min. The results obtained are shown in Table 1.

(Compressive Strength Test)

A sample after mixing was filled in a metal mold provided with a hollow having an inner diameter of 4 mm and a length of 6 mm and press contacted by using a glass sheet via cellophane, to obtain ten cylindrical cured materials. The obtained test pieces were immersed in distilled water at 37° C. for 24 hours and then subjected to a compressive strength test by means of an autograph (made by Shimadzu Corporation) at a crosshead speed of 1 mm/min. The results obtained are shown in Table 1.

EXAMPLE 2

The following components were mixed to prepare a first paste.

| Component (a): | Acrylic acid-itaconic acid copolymer having a weight average molecular weight of 24,000 | 27% by weight |
|---|---|---|
| | Polyacrylic acid having a weight average molecular weight of 16,000 | 30% by weight |
| Component (b): | Distilled water | 26% by weight |
| Component (c): | Silane-modified quartz powder [prepared by adding 20 g of a 10% γ-methacryloxy-propyl trimethoxysilane-ethyl alcohol solution to 100 g of a fine quartz having a mean particle size of 10 μm, stirring the mixture in a | 10% by weight |

| | -continued | |
|---|---|---|
| | mortar, and then drying it at 110° C. for 2 hours by a vapor dryer] | |
| Component (f): | Sodium benzenesulfinate | 7% by weight |

The following components were mixed to prepare a second paste.

| Component (d): | Silane-modified fluoro-aluminosilicate glass powder [prepared by mixing 23 g of aluminum oxide, 41 g of silicic anhydride, 10 g of calcium fluoride, 13 g of calcium phosphate, and 13 g of aluminum phosphate; keeping the mixture in a high-temperature electric furnace at 1,100° C. for 5 hours to melt a glass; after cooling, pulverizing the product in a ball mill for 10 hours; passing the pulverized product through a 200-mesh (ASTM) sieve to form a glass powder; mixing 100 g of the glass powder with 20 g of a 10% vinyl triethoxysilane-ethyl alcohol solution in a mortar; and then drying it at 110° C. for 2 hours by a vapor dryer] | 60% by weight |
|---|---|---|
| Component (e): | Hydroxyethyl methacrylate | 18% by weight |
| | Di-2-methacryloxyethyl-2,2,4-triethylhexamethylene dicarbamate | 12% by weight |
| | Neopentyl glycol dimethacrylate | 10% by weight |

0.8 g of the first paste and 2.3 g of the second paste were weighed and mixed for 10 seconds by using a mixed paper and a spatula. As a result, a working time at room temperature of 23° C. was 2 minutes and 10 seconds. The same mixing operation manner was carried out, and ten samples were subjected to the same tests as in Example 1. The results obtained are shown in Table 1.

EXAMPLE 3

The following components were mixed to prepare a first paste.

| Component (a): | Polyacrylic acid having a weight average molecular weight of 20,000 | 41% by weight |
|---|---|---|
| Component (b): | Distilled water | 21% by weight |
| Component (c): | Silane-modified quartz powder [prepared by adding 20 g of a 10% γ-methacryloxy-propyl trimethoxysilane-ethyl alcohol solution to 100 g of a fine quartz having a mean particle size of 10 μm, stirring the mixture in a mortar, and then drying it at 110° C. for 2 hours by a vapor dryer] | 30% by weight |
| Component (f): | Encapsulated polymerization catalyst having a mean particle | 8% by weight |

-continued

| | | |
|---|---|---|
| | size of 13 μm [prepared by dissolving 5 g of hydroxypropyl-methyl cellulose phthalate in 500 ml of methylene chloride, dispersing therein 10 g of p-toluenesulfonyl chloride having an adjusted mean particle size of 10 μm, and then cooling and drying it under stirring] | |

The following components were mixed to prepare a second paste.

| | | |
|---|---|---|
| Component (d): | Silane-modified fluoro-aluminosilicate glass powder [prepared by mixing 22 g of aluminum oxide, 43 g of silicic anhydride, 12 g of calcium fluoride, 15 g of a calcium phosphate, and 8 g of strontium carbonate; keeping the mixture in a high-temperature electric furnace at 1,200° C. for 5 hours to melt a glass; after cooling, pulverizing the product in a ball mill for 10 hours; passing the pulverized product through a 200-mesh (ASTM) sieve to form a glass powder; mixing 100 g of the glass powder with 20 g of a 10% γ-methacryloxypropyl trimethoxysilane-ethyl alcohol solution in a mortar; and then drying it at 110° C. for 2 hours by a vapor dryer] | 82% by weight |
| Component (e): | Hydroxyethyl methacrylate | 10% by weight |
| | 2-hydroxy-1-acryloxy-3-methacryloxypropane | 3% by weight |
| | 1,6-hexanediol dimethacrylate | 4% by weight |
| Polymerization inhibitor: | Di-t-butylhydroxy-toluene | 1% by weight |

0.8 g of the first paste and 2.3 g of the second paste were weighed and mixed for 10 seconds by using a mixing paper and a spatula. As a result, a working time at room temperature of 23° C. was 2 minutes and 10 seconds. The same mixing operation manner was carried out, and ten samples were subjected to the same tests as in Example 1. The results obtained are shown in Table 1.

EXAMPLE 4

The following components were mixed to prepare a first paste.

| | | |
|---|---|---|
| Component (a): | Polymaleic acid having a weight average molecular weight of 16,000 | 25% by weight |
| | Polyacrylic acid having a weight average molecular weight of 30,000 | 5% by weight |
| Component (b): | Distilled water | 30% by weight |

-continued

| | | |
|---|---|---|
| Component (c): | Silane-modified barium glass powder [prepared by adding 20 g of a 10% vinyl ethoxysilane-ethyl alcohol solution to 100 g of a barium glass powder having a mean particle size of 12 μm, stirring the mixture in a mortar, and then drying it at 110° C. for 2 hours by a vapor dryer] | 32% by weight |
| Component (f): | Encapsulated polymerization catalyst having a mean particle size of 13 μm [prepared by dissolving 5 g of hydroxypropylmethyl cellulose phthalate in 500 ml of methylene chloride, dispersing therein 10 g of sodium benzenesulfinate having an adjusted mean particle size of 10 μm, and then cooling and drying under stirring] | 8% by weight |

The following components were mixed to prepare a second paste.

| | | |
|---|---|---|
| Component (d): | Silane-modified fluoro-aluminosilicate glass powder [prepared by mixing 23 g of aluminum oxide, 41 g of silicic anhydride, 10 g of calcium fluoride, 13 g of calcium phosphate, and 13 g of aluminum phosphate; keeping the mixture in a high-temperature electric furnace at 1,100° C. for 5 hours to melt a glass; after cooling, pulverizing the product in a ball mill for 10 hours; passing the pulverized product through a 200-mesh (ASTM) sieve to form a glass powder; mixing 100 g of the glass powder with 20 g of a 10% vinyl triethoxysilane-ethyl alcohol solution in a mortar; and then drying it at 110° C. for 2 hours by a vapor dryer] | 74% by weight |
| Component (e): | Hydroxyethyl methacrylate | 4% by weight |
| | 2-hydroxy-1-acryloxy-3-methacryloxypropane | 4% by weight |
| | Di-2-methacryloxyethyl-2,2,4-triethylhexamethylene dicarbamate | 15% by weight |
| | Glycidyl methacrylate | 1% by weight |
| Polymerization inhibitor: | Di-t-butylhydroxy-toluene | 2% by weight |

0.8 g of the first paste and 2.3 g of the second paste were weighed and mixed for 10 seconds by using a mixed paper and a spatula. As a result, a working time at room temperature of 23° C. was 1 minute and 55 seconds. The same mixing operation manner was carried out, and ten samples were subjected to the same tests as in Example 1. The results obtained are shown in Table 1.

EXAMPLE 5

The following components were mixed to prepare a first paste.

| | | |
|---|---|---|
| Component (a): | Polymaleic acid having a weight average molecular weight of 16,000 | 19% by weight |
| | Polyacrylic acid having a weight average molecular weight of 24,000 | 19% by weight |
| Component (b): | distilled water | 30% by weight |
| Component (c): | Silane-modified barium glass powder [prepared by adding 20 g of a 10% vinyl ethoxysilane-ethyl alcohol solution to 100 g of a barium glass powder having a mean particle size of 12 $\mu$m, stirring the mixture in a mortar, and then drying it at 110° C. for 2 hours by a vapor dryer] | 32% by weight |

The following components were mixed to prepare a second paste.

| | | |
|---|---|---|
| Component (d): | Silane-modified fluoro-aluminosilicate glass powder [prepared by mixing 23 g of aluminum oxide, 41 g of silicic anhydride, 10 g of calcium fluoride, 13 g of calcium phosphate, and 13 g of aluminum phosphate; keeping the mixture in a high-temperature electric furnace at 1,100° C. for 5 hours to melt a glass; after cooling, pulverizing the product in a ball mill for 10 hours; passing the pulverized product through a 200-mesh (ASTM) sieve to form a glass powder; mixing 100 g of the glass powder with 20 g of a 10% vinyl triethoxysilane-ethyl alcohol solution in a mortar; and then drying it at 110° C. for 2 hours by a vapor dryer] | 71% by weight |
| Component (e): | Hydroxyethyl methacrylate | 4% by weight |
| | 2-hydroxy-1-acryloxy-3-methacryloxypropane | 5% by weight |
| | Di-2-methacryloxyethyl-2,2,4-triethylhexamethylene dicarbamate | 10% by weight |
| Component (f): | Encapsulated polymerization catalyst having a mean particle size of 17 $\mu$m [prepared by dissolving 5 g of hydroxypropylmethyl cellulose phthalate in 500 ml of methylene chloride, dispersing therein 10 g of sodium benzenesulfinate having an adjusted mean particle size of 10 $\mu$m, and then cooling and drying it under stirring to prepare an encapsulated polymerization catalyst having a mean particle size of 13 $\mu$m; and then adding 10 g of that encapsulated polymerization catalyst as a core substance to 500 ml of distilled water having 10 g of polyvinyl alcohol dissolved therein; and then cooling and drying the mixture under stirring] | 10% by weight |
| Polymerization inhibitor: | Di-t-butylhydroxy-toluene | 2% by weight |

1.1 g of the first paste and 1.7 g of the second paste were weighed and mixed for 10 seconds by using a mixing paper and a spatula. As a result, a working time at room temperature of 23° C. was 2 minutes and 10 seconds. The same mixing operation manner was carried out, and ten samples were subjected to the same tests as in Example 1. The results obtained are shown in Table 1.

EXAMPLE 6

The following components were mixed to prepare a first paste.

| | | |
|---|---|---|
| Component (a): | Acrylic acid-itaconic acid copolymer having a weight average molecular weight of 24,000 | 20% by weight |
| Component (b): | Distilled water | 21% by weight |
| Component (c): | Silane-modified silica sand powder [prepared by adding 20 g of a 10% vinyl ethoxysilane-ethyl alcohol solution to 100 g of a fine silica sand having a mean particle size of 4 $\mu$m, stirring the mixture in a mortar, and then drying it at 110° C. for 2 hours by a vapor dryer] | 20% by weight |
| | Silane-modified quartz powder [prepared by adding 20 g of a 10% $\gamma$-methacryloxy-propyl tri-methoxysilane-ethyl alcohol solution to 100 g of a fine quartz having a mean particle size of 10 $\mu$m, stirring the mixture in a mortar, and then drying it at 110° C. for 2 hours by a vapor dryer] | 34% by weight |
| Component (f): | p-toluenesulfonyl fluoride | 5% by weight |

The following components were mixed to prepare a second paste.

| | | |
|---|---|---|
| Component (d): | Silane-modified fluoro-aluminosilicate glass powder [prepared by thoroughly mixing 22 g of aluminum oxide, 43 g of silicic anhydride, 12 g of calcium fluoride, 15 g of calcium phosphate, and 8 g of strontium carbonate; keeping the mixture in a high-temperature electric furnace at 1,200°C. for 5 hours to melt a glass; after cooling, pulverizing the product in a ball mill for 10 hours; | 60% by weight |

-continued

| | | |
|---|---|---|
| | passing the pulverized product through a 200-mesh (ASTM) sieve to form a glass powder; mixing 100 g of the glass powder with 20 g of a 10% γ-methacryloxypropyl trimethoxysilane-ethyl alcohol solution in a mortar; and then drying it at 110° for 2 hours by a vapor dryer] | |
| Component (e): | Hydroxyethyl methacrylate | 3% by weight |
| | 1,3-butanediol dimethacrylate | 7% by weight |
| | Di-2-methacryloxyethyl-2,2,4-triethylhexamethylene dicarbamate | 30% by weight |

0.8 g of the first paste and 2.3 g of the second paste were weighed and mixed for 10 seconds by using a mixing paper and a spatula. As a result, a working time at room temperature of 23° C. was 2 minutes and 00 seconds. The same mixing operation manner was carried out, and ten samples were subjected to the same tests as in Example 1. The results obtained are shown in Table 1.

EXAMPLE 7

The following components were mixed to prepare a first paste.

| | | |
|---|---|---|
| Component (a): | Acrylic acid-itaconic acid copolymer having a weight average molecular weight of 24,000 | 20% by weight |
| Component (b): | Distilled water | 21% by weight |
| Component (c): | Silane-modified silica sand powder [prepared by adding 20 g of a 10% vinyl ethoxysilane-ethyl alcohol solution to 100 g of a fine silica sand having a mean particle size of 4 μm, stirring the mixture in a mortar, and then drying it at 110° C. for 2 hours by a vapor dryer] | 54% by weight |
| Component (f): | Encapsulated polymerization catalyst having a mean particle size of 12 μm [prepared by dissolving 5 g of cellulose acetate phthalate in 500 ml of methylene chloride, dispersing therein 10 g of p-toluenesulfonyl fluoride having an adjusted mean particle size of 10 μm, and then cooling and drying under stirring] | 5% by weight |

The following components were mixed to prepare a second paste.

| | | |
|---|---|---|
| Component (d): | Silane-modified fluoro-aluminosilicate glass powder [prepared by mixing 23 g of aluminum oxide, 41 g of silicic anhydride, | 50% by weight |

-continued

| | | |
|---|---|---|
| | 10 g of calcium fluoride, 13 g of calcium phosphate, and 13 g of aluminum phosphate; keeping the mixture in a high-temperature electric furnace at 1,100° C. for 5 hours to melt a glass; after cooling, pulverizing the product in a ball mill for 10 hours; passing the pulverized product through a 200-mesh (ASTM) sieve to form a glass powder; mixing 100 g of the glass powder with 20 g of a 10% vinyl triethoxysilane-ethyl alcohol solution in a mortar; and then drying it at 110° C. for 2 hours by a vapor dryer] | |
| Component (e): | Hydroxyethyl methacrylate | 10% by weight |
| | Triethylene glycol dimethacrylate | 10% by weight |
| | Di-2-methacryloxyethyl-2,2,4-triethylhexamethylen dicarbamate | 20% by weight |
| | Neopentyl glycol dimethacrylate | 10% by weight |

0.6 g of the first paste and 2.4 g of the second paste were weighed and mixed for 10 seconds by using a mixing paper and a spatula. As a result, a working time at room temperature of 23° C. was 2 minutes and 15 seconds. The same mixing operation manner was carried out, and ten samples were subjected to the same tests as in Example 1. The results obtained are shown in Table 1.

EXAMPLE 8

The following components were mixed to prepare a first paste.

| | | |
|---|---|---|
| Component (a): | Polyacrylic acid having a weight average molecular weight of 20,000 | 35% by weight |
| Component (b): | Distilled water | 37% by weight |
| Component (c): | Silane-modified quartz powder [prepared by adding 20 g of a 10% γ-methacryloxypropyl trimethoxysilane-ethyl alcohol solution to 100 g of a fine quartz having a mean particle size of 10 μm, stirring the mixture in a mortar, and then drying it at 110° C. for 2 hours by a vapor dryer] | 27% by weight |
| Component (f): | camphorquinone | 1% by weight |

The following components were mixed to prepare a second paste.

| | | |
|---|---|---|
| Component (d): | Fluoro-aluminosilicate glass powder [prepared by mixing 22 g of aluminum oxide, 43 g of silicic anhydride, 12 g of calcium fluoride, 15 g of calcium phosphate 1 and 8 g of strontium carbonate; keeping the mixture in a high-temperature electric furnace at 1,200° C. for | 61% by weight |

|                | 5 hours to melt a glass; after cooling, pulverizing the product in a ball mill for 10 hours; passing the pulverized product through a 200-mesh (ASTM) sieve to form a glass powder] | |
|---|---|---|
| Component (e): | Hydroxyethyl methacrylate | 8% by weight |
|                | 2-hydroxy-1-acryloxy-3-methacryloxypropane | 8% by weight |
|                | Di-2-methacryloxyethyl-2,2,4-triethylhexamethylene dicarbamate | 19% by weight |
|                | Glycidyl methacrylate | 2% by weight |
| Component (f): | N,N-dimethylaminoethyl methacrylate | 2% by weight |

0.5 g of the first paste and 2.5 g of the second paste were weighed and mixed for 10 seconds by using a mixing paper and a spatula for the following tests. The results obtained are shown in Table 1.

(Bending Strength Test)

A sample after mixing was filled in an acrylic resin-made tube having an inner diameter of 3 mm and a length of 25 mm, press contacted by using a glass sheet via cellophane, and then irradiated with a light by using a visible light irradiation machine (GC New Light VL-II, manufactured by GC Corporation) for 60 seconds such that the whole was irradiated with the light, to obtain ten cylindrical cured materials. The obtained test pieces were immersed in distilled water at 37° C. for 24 hours and then subjected to a bending strength test by three-point bending by means of an autograph (made by Shimadzu Corporation) at a span of 20 mm and at a crosshead speed of 1 mm/min.

(Compressive Strength Test)

A sample after mixing was filled in a metal mold provided with a hollow having an inner diameter of 4 mm and a length of 6 mm, press contacted by using a glass sheet via cellophane, and then irradiated from one side with a light by using a visible light irradiation machine (GC New Light VL-II, manufactured by GC Corporation) for 60 seconds such that the whole was irradiated with the light, to obtain ten cylindrical cured materials. The obtained test pieces were immersed in distilled water at 37° C. for 24 hours and then subjected to a compressive strength test by means of an autograph (made by Shimadzu Corporation) at a crosshead speed of 1 mm/min.

EXAMPLE 9

The following components were mixed to prepare a first paste.

|                | | |
|---|---|---|
| Component (a): | Polyacrylic acid having a weight average molecular weight of 20,000 | 55% by weight |
| Component (b): | Distilled water | 23% by weight |
| Component (c): | Silane-modified silica sand powder [prepared by adding 20 g of a 10% vinyl ethoxysilane-ethyl alcohol solution to 100 g of fine powdered silica sand having a mean particle size of 4 μm, stirring the mixture in a mortar, and then drying it at 110° C. for 2 hours by a vapor dryer] | 22% by weight |

The following components were mixed to prepare a second paste.

|                | | |
|---|---|---|
| Component (d): | Silane-modified fluoro-aluminosilicate glass powder [prepared by mixing 22 g of aluminum oxide, 43 g of silicic anhydride, 12 g of calcium fluoride, 15 g of calcium phosphate, and 8 g of strontium carbonate; keeping the mixture in a high-temperature electric furnace at 1,200° C. for 5 hours to melt a glass; after cooling, pulverizing the product in a ball mill for 10 hours; passing the pulverized product through a 200-mesh (ASTM) sieve to form a glass powder; mixing 100 g of the glass powder with 20g of a 10% γmethacryloxypropyl trimethoxysilane-ethyl alcohol solution in a mortar; and then drying it at 110° C. for 2 hours by a vapor dryer] | 60% by weight |
| Component (e): | Hydroxyethyl methacrylate | 10% by weight |
|                | 2-hydroxy-1-acryloxy-3-methacryloxypropane | 4% by weight |
|                | Di-2-methacryloxyethyl-2,2,4-triethylhexamethylene dicarbamate | 20% by weight |
|                | 1,3-butanediol methacrylate | 2% by weight |
| Component (f): | Camphorquinone | 2% by weight |
|                | N,N-dimethylaminoethyl methacrylate | 2% by weight |

1.2 g of the first paste and 1.8 g of the second paste were weighed and mixed in the same manner as in Example 8, and ten samples were subjected to the same tests as in Example 8. The results obtained are shown in Table 1.

EXAMPLE 10

The following components were mixed to prepare a first paste.

|                | | |
|---|---|---|
| Component (a): | Polyacrylic acid having a weight average molecular weight of 16,000 | 23% by weight |
| Component (b): | distilled water | 57% by weight |
| Component (c): | Silane-modified quartz powder [prepared by adding 20 g of a 10% γmethacryloxypropyl trimethoxysilane-ethyl alcohol solution to 100 g of a fine quartz having a mean particle size of 10 μm, stirring the mixture in a mortar, and then drying it at 110° C. for 2 hours by a vapor dryer) | 18% by weight |
| Component (f): | Camphorquinone | 1% by weight |
|                | N,N-dimethyl-p-toluidine | 1% by weight |

The following components were mixed to prepare a second paste.

|                | | |
|---|---|---|
| Component (d): | Silane-modified fluoro-aluminosilicate glass powder | 71% by weight |

-continued

| | | |
|---|---|---|
| | [prepared by mixing 23 g of aluminum oxide, 41 g of silicic anhydride, 10 g of calcium fluoride, 13 g of calcium phosphate, and 13 g of aluminum phosphate; keeping the mixture in a high-temperature electric furnace at 1,100° C. for 5 hours to melt a glass; after cooling, pulverizing the product in a ball mill for 10 hours; passing the pulverized product through a 200-mesh (ASTM) sieve to form a glass powder; mixing 100 g of the glass powder with 20 g of a 10% vinyl triethoxy-silane-ethyl alcohol solution in a mortar; and then drying it at 110° C. for 2 hours by a vapor dryer] | |
| Component (e): | Hydroxyethyl methacrylate | 15% by weight |
| | 2-hydroxy-1-acryloxy 3-methacryloxypropane | 12% by weight |
| | Neopentyl glycol dimethacrylate | 2% by weight |

2.3 g of the first paste and 0.8 g of the second paste were weighed and mixed in the same manner as in Example 8, and ten samples were subjected to the same tests as in Example 8. The results obtained are shown in Table 1.

EXAMPLE 11

The following components were mixed to prepare a first paste.

| | | |
|---|---|---|
| Component (a): | Polymaleic acid having a weight average molecular weight of 8,000 | 16% by weight |
| | Polyacrylic acid having a weight average molecular weight of 16,000 | 16% by weight |
| Component (b): | Distilled water | 26% by weight |
| Component (c): | silane-modified quartz powder [prepared by adding 20 g of a 10% γ-methacryloxypropyl trimethoxysilane-ethyl alcohol solution to 100 g of a fine quartz having a mean particle size of 10 μm, stirring the mixture in a mortar, and then drying it at 110° C. for 2 hours by a vapor dryer] | 35% by weight |
| Component (f): | p-toluenesulfonyl fluoride | 6% by weight |
| | Camphorquinone | 1% by weight |
| The following components were mixed to prepare a second paste. | | |
| Component (d): | Fluoro-aluminosilicate glass powder [prepared by mixing 22 g of aluminum oxide, 43 g of silicic anhyddride, 12 g of calcium fluoride, 15 g of calcium phosphate and 8 g of strontium carbonate; keeping the mixture in a high-temperature electric furnace at 1,200° C. for 5 hours to melt a glass; after cooling, pulverizing the product in a ball mill for 10 hours; passing the pulverized product through a 200-mesh (ASTM) sieve to form a glass powder] | 76% by weight |
| Component (e): | Hydroxyethyl methacrylate | 4% by weight |
| | 1,6-hexanediol dimethacrylate | 11% by weight |
| | 2-hydroxy-1-acryloxy-3-methacryloxypropane | 7% by weight |
| Polymerization inhibitor: | Di-t-butylhydroxy-toluene | 2% by weight |

1.2 g of the first paste and 1.8 g of the second paste were weighed and mixed for 10 seconds by using a mixing paper and a spatula. As a result, a working time at room temperature of 23° C. was 1 minute and 55 seconds. The same mixing operation was carried out, and ten samples were subjected to the same tests as in Example 1. The results obtained are shown in Table 1.

EXAMPLE 12

The following components were mixed to prepare a first paste.

| | | |
|---|---|---|
| Component (a): | Polyacrylic acid having a weight average molecular weight of 20,000 | 33% by weight |
| Component (b): | Distilled water | 34% by weight |
| Component (c): | Silane-modified quartz powder [prepared by adding 20 g of a 10% γ-methacryloxypropyl trimethoxysilane-ethyl alcohol solution to 100 g of a fine quartz having a mean particle size of 10 μm, stirring the mixture in a mortar, and then drying it at 110° C. for 2 hours by a vapor dryer] | 26% by weight |
| Component (f): | Encapsulated polymerization catalyst having a mean particle size of 13 μm [prepared by dissoiving 5 g of hydroxypropylmethyl cellulose phthalate in 500 ml of methylene chloride, dispersing therein 10 g of p-toluenesulfonyl chloride having an adjusted mean particle size of 10 μm, and then cooling and drying under stirring] | 7% by weight |
| The following components were mixed to prepare a second paste | | |
| Component (d): | Silane-modified fluoro-aluminosilicate glass powder [prepared by mixing 22 g of aluminum oxide, 43 g of silicic anhydride, 12 g of calcium fluoride, 15 g of calcium phosphate, and 8 g of strontium carbonate; keeping the mixture in a high-temperature electric furnace at 1,200° C. for 5 hours to melt a glass; after cooling, pulverizing the | 72% by weight |

-continued

| | | |
|---|---|---|
| | product in a ball mill for 10 hours; passing the pulverized product through a 200-mesh (ASTM) sieve to form a glass powder; mixing 100 g of the glass powder with 20 g of a 10% γ-methacryloxypropyl trimethoxysilane-ethyl alcohol solution in a mortar; and then drying it at 110° C. for 2 hours by a vapor dryer] | |
| Component (e): | Hydroxyethyl methacrylate | 4% by weight |
| | 2-hydroxy-1-acryloxy-3-methacryloxypropane | 4% by weight |
| | Di-2-methacryloxyethyl-2,2,4-triethylhexamethylene dicarbamate | 15% by weight |
| | Glycidyl methacrylate | 1% by weight |
| Component (f): | Camphorquinone | 2% by weight |
| Polymerization inhibitor: | Di-t-butylhydroxy-toluene | 2% by weight |

0.8 g of the first paste and 2.3 g of the second paste were weighed and mixed for 10 seconds by using a mixing paper and a spatula. As a result, a working time at room temperature of 23° C. was 2 minutes and 15 seconds.

Next, 0.8 g of the first paste and 2.3 g of the second paste were weighed and mixed in the same manner as in Example 1, and ten samples were subjected to the same tests as in Example 8. The results obtained are shown in Table 1.

EXAMPLE 13

The following components were mixed to prepare a first paste.

| | | |
|---|---|---|
| Component (a): | Polyacrylic acid having a weight average molecular weight of 24,000 | 31% by weight |
| Component (b): | Distilled water | 37% by weight |
| Component (c): | Silane-modified quartz powder [prepared by adding 20 g of a 10% γ-methacryloxypropyl trimethoxysilane-ethyl alcohol solution to 100 g of a fine quartz having a mean particle size of 10 μm, stirring the mixture in a mortar, and then drying it at 110° C. for 2 hours by a vapor dryer] | 30% by weight |
| Component (f): | Camphorquinone | 2% by weight |

The following components were mixed to prepare a second paste.

| | | |
|---|---|---|
| Component (d): | Silane-modified fluoro-aluminosilicate glass powder [prepared by mixing 22 g of aluminum oxide, 43 g of silicic anhydride, 12 g of calcium fluoride, 15 g of calcium phosphate, and 8 g of strontium carbonate; keeping the mixture in a high-temperature electric furnace at 1,200° C. for 5 hours to melt a glass; after cooling, pulverizing the product in a ball mill for 10 hours; | 65% by weight |

-continued

| | | |
|---|---|---|
| | passing the pulverized product through a 200-mesh (ASTM) sieve to form a glass powder; mixing 100 g of the glass powder with 20 g of a 10% γ-methacryloxypropyl trimethoxysilane-ethyl alcohol solution in a mortar; and then drying it at 110° C. for 2 hours by a vapor dryer] | |
| Component (e): | Hydroxyethyl methacrylate | 5% by weight |
| | 2-hydroxy-1-acryloxy-3-methacryloxypropane | 5% by weight |
| | Di-2-methacryloxyethyl-2,2,4-triethylhexamethylene dicarbamate | 15% by weight |
| | Glycidyl methacrylate | 1% by weight |
| Component (f): | Encapsulated polymerization catalyst having a mean particle size of 20 μm [prepared by dissolving 5 g of hydroxypropylmethyl cellulose phthalate in 500 ml of methylene chloride, dispersing therein 10 g of p-toluenesulfonyl chloride having an adjusted mean particle size of 13 μm, and then cooling and drying it under stirring to prepare an encapsulated polymerization catalyst having a mean particle size of 13 μm; and then adding 9 g of that encapsulated polymerization catalyst as a core substance to 500 ml of distilled water having 10 g of carboxymethyl cellulose dissolved therein; and then cooling and drying the mixture under stirring] | 7% by weight |
| polymerization inhibitor: | Di-t-butylhydroxy-toluene | 2% by weight |

0.6 g of the first paste and 2.4 g of the second paste were weighed and mixed for 10 seconds by using a mixing paper and a spatula. As a result, a working time at room temperature of 23° C. was 2 minutes and 15 seconds. The same mixing operation was carried out, and ten samples were subjected to the same tests as in Example 1. The results obtained are shown in Table 1.

EXAMPLE 14

The following components were mixed to prepare a first paste.

| | | |
|---|---|---|
| Component (a): | Polymaleic acid having a weight average molecular weight of 16,000 | 20% by weight |
| | Polyacrylic acid having a weight average molecular weight of 30,000 | 5% by weight |
| Component (b): | Distilled water | 25% by weight |
| Component (c): | Silane-modified barium glass powder [prepared by adding 20 g of a 10% vinyl ethoxysilane-ethyl alcohol solution to 100 g of a barium glass powder having a mean particle size of 12 μm, stirring the mixture in a mortar, and | 42% by weight |

-continued

| | | |
|---|---|---|
| | then drying it at 110° C. for 2 hours by a vapor dryer] | |
| Component (f): | Encapsulated polymerization catalyst having a mean particle size of 13 μm [prepared by dissolving 5 g of hydroxypropylmethyl cellulose phthalate in 500 ml of methylene chloride, dispersing therein 10 g of sodium benzensulfinate having an adjusted mean particle size of 10 μm, and then cooling and drying under stirring] | 8% by weight |

The following components were mixed to prepare a second paste.

| | | |
|---|---|---|
| Component (d): | Silane-modified fluoro-aluminosilicate glass powder [prepared by mixing 23 g of aluminum oxide, 41 g of silicic anhydride, 10 g of calcium fluoride, 13 g of calcium phosphate, and 13 g of aluminum phosphate; keeping the mixture in a high-temperature electric furnace at 1,100° C. for 5 hours to melt a glass; after cooling, pulverizing the product in a ball mill for 10 hours; passing the pulverized product through a 200-mesh (ASTM) sieve to form a glass powder; mixing 100 g of the glass powder with 20 g of a 10% vinyl triethoxysilane-ethyl alcohol solution in a mortar; and then drying it at 110° C. for 2 hours by a vapor dryer] | 68% by weight |
| Component (e): | Hydroxyethyl methacrylate | 5% by weight |
| | 1,6-hexanediol dimethacrylate | 15% by weight |
| | 1,3-butanediol dimethacrylate | 7% by weight |
| Component (f): | Camphorquinone | 2% by weight |
| | Triethanolamine | 1% by weight |
| Polymerization inhibitor: | Di-t-butylhydroxy-toluene | 2% by weight |

2.4 g of the first paste and 0.6 g of the second paste were weighed and mixed for 10 seconds by using a mixing paper and a spatula. As a result, a working time at room temperature of 23° C. was 2 minute and 00 seconds. The same mixing operation was carried out, and ten samples were subjected to the same tests as in Example 1. The results obtained are shown in Table 1.

EXAMPLE 15

The following components were mixed to prepare a first paste.

| | | |
|---|---|---|
| Component (a): | Polymaleic acid having a weight average. molecular weight of 8,000 | 45% by weight |
| | Polyacrylic acid having a weight average molecular weight ot 16,000 | 5% by weight |
| Component (b): | Distilled water | 25% by weight |
| Component (c): | Silane-modified quartz powder [prepared by adding 20 g of a 10% | 20% by weight |

-continued

| | | |
|---|---|---|
| | γ-methacryloxypropyl trimethoxysilane-ethyl alcohol solution to 100 g of a fine quartz having a mean particle size of 10 μm, stirring the mixture in a mortar, and then drying it at 110° C. for 2 hours by a vapor dryer] | |
| Component (f): | p-toluenesulfonyl fluoride | 3% by weight |
| | Camphorquinone | 1% by weight |
| | Triethanolamine | 1% by weight |

The following components were mixed to prepare a second paste.

| | | |
|---|---|---|
| Component (d): | Silane-modified fluoro-aluminosilicate glass powder [prepared by mixing 22 g of aluminum oxide, 43 g of silicic anhydride, 12 g of calcium fluoride, 15 g of calcium phosphate, and 8 g of strontium carbonate; keeping the mixture in a high-temperature electric furnace at 1,200° C. for 5 hours to melt a glass; after cooling, pulverizing the product in a ball mill for 10 hours; passing the pulverized product through a 200-mesh (ASTM) sieve to form a glass powder; mixing 100 g of the glass powder with 20 g of a 10% γ-methacryloxypropyl trimethoxysilane-ethyl alcohol solution in a mortar; and then drying it at 110° C. for 2 hours by a vapor dryer] | 72% by weight |
| Component (e): | Hydroxyethyl methacrylate | 6% by weight |
| | 1,6-hexanediol dimethacrylate | 10% by weight |
| | Di-2-mehtacryloxyethyl-2,2,4-triethylhexamethylene dicarbamate | 8% by weight |
| Component (f): | Camphorquinone | 2% by weight |
| | N,N-dimethylaminoethyl methacrylate | 2% by weight |

1.5 g of the first paste and 1.5 g of the second paste were weighed and mixed for 10 seconds by using a mixing paper and a spatula. As a result, a working time at room temperature of 23° C. was 1 minute and 52 seconds.

Next, 1.5 g of the first paste and 1.5 g of the second paste were weighed and mixed in the same manner as in Example 8, and ten samples were subjected to the same tests as in Example 8. The results obtained are shown in Table 1.

Comparative Example 1

"Fuji I" (made by GC Corporation) was used as a conventional glass ionomer cement. 1.8 g of a cement powder and 1.0 g of a liquid were weighed on a mixing paper, and the powder component was divided into one group of 1/2 and two groups of 1/4 by using a spatula. First, one group of 1/4 was mixed with the whole of the liquid for 5 seconds, and another group of 1/4 was then added thereto, followed by mixing the mixture for 10 seconds. Finally, the group of 1/2 was mixed for 15 seconds, and a mixing operation was further carried out for 10 seconds, whereby the powder component and the liquid component were thoroughly mixed with each other. A working time was 2 minutes and 00 seconds at room temperature of 23° C. The same mixing was carried out, and ten samples were subjected to the same tests as in Example 1. The results obtained are shown in Table 1.

Comparative Example 2

"Fuji II LC" (made by GC Corporation) was used a conventional photocuring type glass ionomer cement. 2.0 g of a cement powder and 1.0 g of a liquid were weighed on a mixing paper, and the powder component was divided into one group of 1/2 and two groups of 1/4 by using a spatula. First, one group of 1/4 was mixed with the whole of the liquid for 5 seconds, and another group of 1/4 was then added thereto, followed by mixing the mixture for 10 seconds. Finally, the group of 1/2 was mixed for 15 seconds, and a mixing operation was further carried out for 10 seconds, whereby the powder component and the liquid component were thoroughly mixed with each other. A working time was 3 minutes and 30 seconds at room temperature of 23° C. The same mixing was carried out, and ten samples were subjected to the same tests as in Example 8. The results obtained are shown in Table 1.

TABLE 1

| | Mixing Time (sec) | Working Time (min & sec) | Bending Strength (Mpa) | Compressive Strength (Mpa) |
|---|---|---|---|---|
| Example 1 | 10 | 2' 25" | 71 ± 3 | 166 ± 4 |
| Example 2 | 10 | 2' 10" | 77 ± 5 | 187 ± 8 |
| Example 3 | 10 | 2' 10" | 83 ± 5 | 202 ± 6 |
| Example 4 | 10 | 1' 55" | 98 ± 6 | 217 ± 6 |
| Example 5 | 10 | 2' 10" | 87 ± 6 | 195 ± 5 |
| Example 6 | 10 | 2' 00" | 104 ± 4 | 215 ± 6 |
| Example 7 | 10 | 2' 15" | 102 ± 5 | 205 ± 5 |
| Example 8 | 10 | — | 85 ± 5 | 193 ± 5 |
| Example 9 | 10 | — | 102 ± 3 | 201 ± 4 |
| Example 10 | 10 | — | 69 ± 5 | 177 ± 6 |
| Example 11 | 10 | 1' 55" | 65 ± 5 | 168 ± 5 |
| Example 12 | 10 | 2' 15" | 95 ± 4 | 198 ± 6 |
| Example 13 | 10 | 2' 15" | 92 ± 4 | 190 ± 5 |
| Example 14 | 10 | 2' 00" | 67 ± 4 | 175 ± 6 |
| Example 15 | 10 | 1' 52" | 84 ± 4 | 184 ± 6 |
| Comparative Example 1 | 40 | 2' 00" | 5 ± 5 | 168 ± 39 |
| Comparative Example 2 | 40 | 3' 30" | 49 ± 11 | 173 ± 25 |

As described above in detail, the paste-type dental glass ionomer composition according to the present invention comprises a first paste and a second paste. By the construction wherein the both pastes are mixed to effect curing, it has been confirmed that the complicated mixing operation required to have a skill, which was carried out in a conventional dental glass ionomer cement using a powder component and a liquid component, is not required, the mixing can be effected uniformly within a shorter period of mixing time, the working time and compressive strength equal to those in the conventional technology can be given, and that the bending strength is particularly superior. Thus, it should be clear that the present invention can greatly contribute to the dental field.

While the invention has been described in detail and with reference to specific embodiments thereof, it will be apparent to one skilled in the art that various changes and modifications can be made therein without departing from the spirit and scope thereof.

What is claimed is:

1. A paste-type dental glass ionomer cement composition comprising a first paste comprising an $\alpha$-$\beta$ unsaturated carboxylic acid polymer, water, and a filler not reactive with said $\alpha$-$\beta$ unsaturated carboxylic acid polymer; and a second paste comprising a fluoroaluminosilicate glass powder and a polymerizable monomer free of an acid group, wherein at least one of said first paste and said second paste contains an encapsulated polymerization catalyst.

2. A paste-type dental glass ionomer cement composition as claimed in claim 1, wherein said first paste comprises 20~60% by weight of an $\alpha$-$\beta$ unsaturated carboxylic acid polymer, 20~60% by weight of water, and 10~60% by weight of a filler not reactive with said $\alpha$-$\beta$ unsaturated carboxylic acid polymer; said second paste comprises 50~85% by weight of a fluoroaluminosilicate glass powder and 15~50% by weight of a polymerizable monomer free of an acid group; and at least one of said first paste and said second paste contains a polymerization catalyst in an amount in total of 0.05~10% by weight based on a total amount of said paste-type dental glass ionomer cement composition in mixing for using said first paste and said second paste.

3. A paste-type dental glass ionomer cement composition as claimed in claim 1, wherein said $\alpha$-$\beta$ unsaturated carboxylic acid polymer is a copolymer or homopolymer of at least one member selected from the group consisting of acrylic acid, methacrylic acid, 2-chloroacrylic acid, 3-chloroacrylic acid, aconitic acid, mesaconic acid, maleic acid, itaconic acid, fumaric acid, glutaconic acid, and citraconic acid and is a polymer not containing a polymerizable ethylenically unsaturated double bond and having a weight average molecular weight of from 5,000 to 40,000.

4. A paste-type dental glass ionomer cement composition as claimed in claim 1, wherein said filler not reactive with said $\alpha$-$\beta$ carboxylic acid polymer is at least one member selected from the group consisting of silica sand, quartz, colloidal silica, feldspar, alumina, strontium glass, barium glass, borosilicate glass, kaolin, talc, calcium carbonate, calcium phosphate, titania, and barium sulfate and has a mean particle size of 0.02~10 μm.

5. A paste-type dental glass ionomer cement composition as claimed in claim 1, wherein said filler not reactive with said $\alpha$-$\beta$ unsaturated carboxylic acid polymer is modified with a polymerizable ethylenically unsaturated double bond-containing organic compound.

6. A paste-type dental glass ionomer cement composition as claimed in claim 1, wherein said fluoroaluminosilicate glass powder is a fluoroaluminosilicate glass powder having a mean particle size of 0.02~10 μm and a specific gravity of 2.4~4.0 and containing $Al^{3+}$, $Si^{4+}$, $F^-$, and $O^{2-}$ as major components and further containing $Sr^{2+}$ and/or $Ca^{2+}$.

7. A paste-type dental glass ionomer cement composition as claimed in claim 1, wherein said fluoroaluminosilicate glass powder has a constitution such that the proportions of $Al^{3+}$, $Si^{4+}$, $F^-$ and a sum of $Sr^{2+}$ and $Ca^{2+}$ are from 10 to 21% by weight, from 9 to 24% by weight, from 1 to 20% by weight, and from 10 to 34% by weight, respectively based on the total weight of the glass.

8. A paste-type dental glass ionomer cement composition as claimed in claim 1, wherein said polymerizable monomer free of an acid group is a polymerizable unsaturated compound containing at least one $CH_2{=}CR{-}COO{-}$ group, wherein R is H or $CH_3$.

9. The paste-type dental glass ionomer cement composition of claim 1, wherein said polymerization catalyst is encapsulated in a water-insoluble polymeric compound.

10. The paste-type dental glass ionomer cement composition of claim 1, wherein said polymerization catalyst is encapsulated in a water-soluble polymeric compound.

11. The paste-type dental glass ionomer cement composition of claim 1, wherein said polymerization catalyst comprises an organic aromatic compound containing at least one $-SO_2-$ group.

* * * * *